(12) United States Patent
Tournier-Couturier

(10) Patent No.: US 11,903,995 B2
(45) Date of Patent: *Feb. 20, 2024

(54) ARTHROFACTIN FOR THE TREATMENT OF ACNE

(71) Applicant: L'OREAL, Paris (FR)

(72) Inventor: Lucie Tournier-Couturier, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 92 days.

This patent is subject to a terminal disclaimer.

(21) Appl. No.: 17/506,994

(22) Filed: Oct. 21, 2021

(65) Prior Publication Data

US 2022/0040256 A1 Feb. 10, 2022

Related U.S. Application Data

(62) Division of application No. 16/470,707, filed as application No. PCT/EP2017/083164 on Dec. 15, 2017, now abandoned.

(30) Foreign Application Priority Data

Dec. 22, 2016 (FR) ...................................... 1663230

(51) Int. Cl.
   *A61K 38/12* (2006.01)
   *A61P 17/10* (2006.01)
   *A61K 9/00* (2006.01)

(52) U.S. Cl.
   CPC ............ *A61K 38/12* (2013.01); *A61K 9/0014* (2013.01); *A61P 17/10* (2018.01)

(58) Field of Classification Search
   None
   See application file for complete search history.

(56) References Cited

U.S. PATENT DOCUMENTS 5,344,913 A 9/1994 Imanaka et al.
2020/0022894 A1* 1/2020 Santos ................ A61K 8/0295

FOREIGN PATENT DOCUMENTS

| FR | 2 898 049 A1 | 9/2007 | |
| WO | WO 99/62482 A1 | 12/1999 | |
| WO | WO-9962482 A1 * | 12/1999 | ........... A61K 8/0212 |
| WO | WO 2018/115522 A1 | 6/2018 | |
| WO | WO-2018115522 A1 * | 6/2018 | ............. A61K 38/12 |

OTHER PUBLICATIONS

Rodrigues et al. "Biosurfactants: potential applications in medicine" J. Antimicrobial Chemotherapy 57:609-618. (Year: 2006).*
Anonymous "Acne Pads Topical" WebMD http://www.webmd.com:80/drugs/2/drug-61727/acne-pads-topical/details (Year: 2014).*
Ryu et al. "Suppression of Propionibacterium acnes Infection and the Associated Inflammatory Response by the Antimicrobial Peptide P5 in Mice" PLoS ONE 7:e0132619. (Year: 2015).*
Lange et al. "Predicting the Structure of Cyclic Lipopeptides by Bioinformatics: Structure Revision of Arthrofactin" ChemBioChem 13:2671-2675. (Year: 2012).*
Katrin Reder-Christ et al., "Model membrane studies for characterization of different activities antibiotic activities of lipopeptides from", Biochimica Biophysica Acta (BBA)—Biomembranes, vol. 1818, No. 3, Aug. 2, 2011, pp. 566-573. XP028397667.
"Final Report on the Safety Assessment of Ethyl Acetate and Butyl Acetate" J. Amer. College of Toxicology 8:681-705. (Year: 1989).

* cited by examiner

*Primary Examiner* — Sudhakar Katakam
*Assistant Examiner* — Zachary J Miknis
(74) *Attorney, Agent, or Firm* — POLSINELLI PC

(57) ABSTRACT

The present invention relates to a mixture of arthrofactin or of a composition containing it and to the use thereof for the treatment of acneic skin.

20 Claims, No Drawings

ARTHROFACTIN FOR THE TREATMENT OF ACNE

The present invention relates to the use of a mixture of arthrofactins in the field of caring for keratin materials such as the skin, and in particular as an agent for treating acneic skin and in particular acneic skin having imperfections related to *P. acnes*.

The invention relates to a method for treating acneic skin using a composition comprising a mixture of arthrofactins.

Common acne is a multifactor disease (face, shoulder region, arms and intertriginous regions). It is the main cause of the most common forms of dermatosis. It is important not to trivialize this disease and to treat it correctly, since it can have debilitating psychosocial consequences, in particular because of the formation of scars.

In its mildest form, it affects almost every human being. Its frequency is maximal at the age of puberty, but it can manifest itself for the first time from the age of 7 to 9, and may extend beyond the age of 40. It is common to still be suffering from acne after the age of 25. Moreover acne affects men as well as women.

Acne is a disease of the sebaceous gland of the follicle. The following pathogenic factors play a determining role in the formation of acne:
  Genetic predisposition.
  Androgens.
  Abnormally increased keratinization (keratinization disorder) in the infundibular portion of the hair follicle.

Indeed, in the deepest parts of the infundibulum, the formation of a larger than normal amount of keratinocytes is noted. These cells differentiate into horny cells which gradually block the lumen of the follicular canal. The physiological process of continuous desquamation from the acro-infundibulum to the surface is disrupted by the increased adhesion of the horny cells produced. A hyperkeratotic plug constituting the comedone, the initial lesion of acne, forms.

Bacterial infections responsible for the hydrolysis of free fatty acids and inflammatory phenomena (papules and pustules).

The predominant three local microorganisms, *Staphylococcus epidermidis*, *Malassezia furfur* and *Propionibacterium acnes*, find an ideal nutritive environment in the sebaceous follicle.

The clinical manifestations are characterized by a polymorphic picture. Interest is focussed here on the most common forms of acne, namely, comedonal acne (juvenile acne), papulo-pustular acne and/or nodular acne.

The retention lesions may be of open or closed comedone type (microcyst, microcomedone, whitehead). The inflammatory lesions derived from the retention lesions may be of the type such as papules, pustules, with indurated nodules, abscesses, fistulas or scar forms.

Evaluation Using the ECLA Scale

The clinical severity of acne has been determined using the semi-quantitative scoring scale ECLA [acne lesion clinical evaluation scale].

This scale is made up of three factors:

TABLE I

Presentation of the ECLA scale

Factor 1 (F1): acne type and intensity; count on the the whole face

| | | Absent = 0 | Scarce = 1 | Low = 2 | Medium = 3 | High = 4 | Very high = 5 | F1 |
|---|---|---|---|---|---|---|---|---|
| R | Open and closed comedones (microcysts) | None | <5 | 5 to 9 | 10 to 19 | 20 to 40 | >40 | R |
| Is | Papules and pustules | None | <5 | 5 to 9 | 10 to 19 | 20 to 40 | >40 | Is |
| Ip | Inflammatory nodules and cysts | None | 1 | 2 | 3 | 4 | ≠5 | Ip |
| Score 1= | | | | | | | | |

Factor 2 (F2): extension and intensity of the acne; beyond the face.

| | | 0 Absent | 1 Low | 2 Medium | 3 High | F2 |
|---|---|---|---|---|---|---|
| Neck (N) | Top cervical zone Bottom cervical zone | | | | | N |
| Chest (C) | | | | | | C |
| Back (B) | Top point of shoulder blade Bottom point of shoulder blade | | | | | B |
| Arm (A) | | | | | | A |
| Score 2= | | | | | | |

Factor 3 (F3): scars - absent = 0; present = 1

| Inflammatory | Non-inflammatory | Excoriations |
|---|---|---|
| IS | NIS | E |

Score 3=
Final score: Score 1 + Score 2 + Score 3 =
The ECLA score is therefore between 0 and 36

For the purposes of the invention, the term "skin" is intended to denote the entire epidermis of the human body. More particularly, the skin considered in the present invention is preferably the skin of the face, of the neckline, of the back or of the scalp, and preferably the skin of the face.

The expression "imperfections related to *Propionibacterium acnes*" is understood to mean open and/or closed comedones, microcysts, papules, pustules and also inflammatory nodules and cysts.

For the purposes of the invention, the term "treatment" is understood to mean curative and/or prophylactic treatment and preferably a curative treatment.

For the purposes of the invention, the term "acneic skin" is intended to mean skin exhibiting acne with an ECLA score of between 1 and 36.

To combat acne, various compounds have already been proposed, which, by topical application to the skin, are capable of reducing the proliferation of *P. acnes*.

Unfortunately, the treatments currently available are not completely satisfactory, in particular from the viewpoint of the side effects which are frequently associated therewith, such as irritative side effects with certain topical agents, for instance retinoids and benzoyl peroxides. Moreover, resistance of *P. acnes* to certain local antibacterial therapies is frequently observed.

There remains therefore the need for topically applied active agents which have an effect on the pathologies related to microorganisms of the *Propionibacterium* genus, and particularly *Propionibacterium acnes*, while at the same time not having the drawbacks of the compounds known for this use.

Moreover, the development of resistance of *P. acnes* against existing active agents reveals the need to identify new molecules in order to maintain over time an effective action on the inhibition of *P. acnes* growth.

Furthermore, there is an additional interest in having available biomolecules of biotechnological origin that are cosmetically active. Very few biomolecules of this type have however been proposed to date, in particular for the treatment of acneic skin.

The Applicant has demonstrated that by using a treatment method that consists in applying to acneic skin and in particular acneic skin having imperfections related to the microorganism *P. acnes*, a composition comprising a mixture of arthrofactins, such a treatment method exhibits activity on the decrease or inhibition of microorganisms involved in the development of acne, especially *Propionibacterium acnes*.

The Applicant has indeed observed that a mixture of arthrofactins according to the invention had a strong inhibitory activity on the growth of *Propionibacterium acnes*, and could therefore be used in a dermatological composition for the treatment of acneic skin.

One subject of the present invention is therefore a method for treating acneic skin and in particular acneic skin having imperfections related to *Propionibacterium acnes*, comprising the application to the acneic skin of a dermatological composition comprising, in a physiologically acceptable medium, at least one mixture of arthrofactins.

One subject of the invention is a mixture of arthrofactin or of a dermatological composition containing at least one mixture of arthrofactin for treating acneic skin and in particular acneic skin having imperfections related to microorganisms of the *Propionibacterium* genus, and particularly *Propionibacterium acnes*.

The present invention results from the unexpected discovery by the inventors that arthrofactin, a partially cyclic lipopeptide of the family of biosurfactants described in Lange et al. (2012) *ChemBioChem* 13:2671-2675 and produced by *Pseudomonas* sp MIS 38 (Morikawa et al. (1993) *J. Bacteriol.* 175:6459-6466), and more particularly a mixture of arthrofactins produced by *Pseudomonas* sp MIS 38, inhibits the proliferation of *P. acnes*, demonstrating an effect on acneic skin.

The mixture of arthrofactins produced by *Pseudomonas* sp MIS 38 as described below makes it possible especially to provide, while at the same time having an effect of treating acneic skin, compositions that have good stability and/or that remain pleasant for the consumer, i.e. being sparingly tacky, having a pleasant feel, and/or having no discomfort sensations such as tautness.

The inventors discovered that the mixture of arthrofactins produced by *Pseudomonas* sp MIS 38 as described below was a good agent for treating acneic skin, and in particular acneic skin having imperfections related to *P. acnes*, this mixture having an effect of inhibiting the growth of *P. acnes*.

Patent FR2898049 describes a cosmetic lip care method comprising the application to the lips of a composition comprising an emulsion of oil in a polar phase, said emulsion comprising at least one cyclic lipopeptide capable of being obtained by fermentation of prokaryotes, the cyclic lipopeptide acting as emulsifier for stabilizing the emulsion. No anti-acne property of arthrofactin is however described in this document.

International application WO9962482 itself describes a surfactant for use in the external preparation of skin comprising a lipopeptide derived from prokaryotes and having low skin penetrability and low skin irritability. No anti-acne property of arthrofactin is however described in this document.

One subject of the present invention is therefore a method for treating acneic skin and in particular acneic skin having imperfections related to *P. acnes* microorganisms, comprising the application to the acneic skin of a dermatological composition comprising, in a physiologically acceptable medium, at least one mixture of arthrofactins, said mixture of arthrofactins comprising:

(i) arthrofactin A of formula (I) below:

$$R_1\text{-D-Leu}_1\text{-D-Asp}_2\text{-D-allo-Thr}_3\text{-D-Leu}_4\text{-D-Leu}_5\text{-D-Ser}_6\text{-L-Leu}_7\text{-D-Ser}_8\text{-L-Ile}_9\text{-L-Ile}_{10}\text{-L-Asp}_{11} \quad (I),$$

in which
the hydroxyl group of the D-allo-Thr$_3$ amino acid residue forms an ester bond with the C-terminal carboxyl group of the L-Asp$_{11}$ amino acid residue, and
R$_1$ represents the group of formula (I') below:

$$\begin{array}{c} \text{O} \quad \text{OH} \\ \| \quad | \\ \text{--C--C--R}_1{'} \\ \text{H}_2 \quad \text{H} \end{array} \quad (I')$$

where R$_1{'}$ is a saturated alkyl chain of 5 to 8 carbon atoms; and (ii) at least one derivative of arthrofactin A, said derivative being of formula (II) below:

$$R\text{-Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11} \quad (II)$$

in which
Xaa$_1$, Xaa$_4$, Xaa$_5$, Xaa$_7$, Xaa$_9$ and Xaa$_{10}$ each represent, independently, D-Leu, L-Leu, D-Ile or L-Ile, Xaa$_2$ and Xaa$_{11}$ each represent, independently, D-Asp, L-Asp, D-Glu or L-Glu, Xaa$_3$ represents D-Thr, L-Thr, D-allo-Thr or L-allo-Thr, Xaa$_6$ and Xaa$_8$ each represent, independently, D-Ser, L-Ser, D-Gln or L-Gln, the hydroxyl group of the Xaa$_3$ amino acid residue forms an ester bond with the C-terminal carboxyl group of the Xaa$_{11}$ amino acid residue, and R represents the group of formula (II') below:

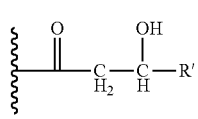

where R' is a hydrocarbon chain of 5 to 9 carbon atoms, optionally comprising at least one ethylenic unsaturation of cis or trans configuration;

for the treatment of acneic skin.

The composition comprising said arthrofactin mixture is intended for topical application to the skin and in particular to the skin of the face.

According to one particular variant of the invention, the composition for treating acneic skin and in particular acneic skin having imperfections related to *Propionibacterium acnes*, additionally comprises a physiologically acceptable medium and at least one compound chosen from thickeners, preservatives, fragrances, bactericides, pigments, colorants, organic solvents including in particular C$_1$-C$_6$ alcohols and C$_2$-C$_{10}$ carboxylic acid esters, carbon-based and/or silicone oils whether they are of mineral, animal and/or plant origin, waxes, fillers, emulsifiers, co-emulsifiers, photoprotective agents which are active in the UV-A and/or UV-B regions, also referred to as UV screening agents, polymers, and hydrophilic or lipophilic gelling agents.

According to one particular embodiment, one subject of the present invention is a method for treating acneic skin and in particular acneic skin having imperfections related to *Propionibacterium acnes*, comprising the application to the acneic skin of a dermatological composition comprising, in a physiologically acceptable medium, at least one mixture of arthrofactins, said mixture of arthrofactins comprising: (i) arthrofactin A of formula (I) as described above and (ii) at least one derivative of arthrofactin A, said derivative being of formula (II) as described above, the composition additionally comprising a physiologically acceptable medium and at least one compound chosen from thickeners, preservatives, fragrances, bactericides, organic solvents including in particular C$_1$-C$_6$ alcohols and C$_2$-C$_{10}$ carboxylic acid esters, and carbon-based and/or silicone oils whether they are of mineral, animal and/or plant origin.

The mixture of arthrofactins as defined below, or the compositions comprising it, may be used once or repeatedly, such as one to two times per day for example, preferably over a period of at least one week, and more particularly of at least four weeks.

DETAILED DESCRIPTION OF THE INVENTION

The mixture of arthrofactins according to the invention, having the anti-acne properties described here, is a mixture of arthrofactins comprising (i) arthrofactin A of formula (I) below:

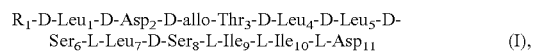

in which the hydroxyl group of the D-allo-Thr$_3$ amino acid residue forms an ester bond with the C-terminal carboxyl group of the L-Asp$_{11}$ amino acid residue, and Another subject of the present invention is a method for preventing and/or treating skin disorders related to *Propionibacterium acnes*, comprising the application to the acneic skin of a dermatological composition comprising, in a physiologically acceptable medium, at least one mixture of arthrofactins, said mixture of arthrofactins comprising: (i) arthrofactin A of formula (I) below:

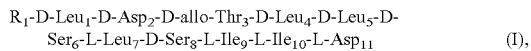

in which the hydroxyl group of the D-allo-Thr$_3$ amino acid residue forms an ester bond with the C-terminal carboxyl group of the L-Asp$_{11}$ amino acid residue, and R$_1$ represents the group of formula (I') below:

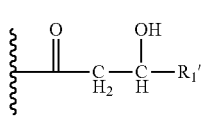

where R$_1$' is a saturated alkyl chain of 5 to 8 carbon atoms; and (ii) at least one derivative of arthrofactin A, said derivative being of formula (II) below:

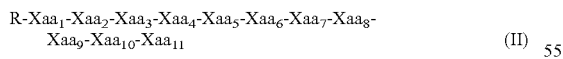

in which

Xaa$_1$, Xaa$_4$, Xaa$_5$, Xaa$_7$, Xaa$_9$ and Xaa$_{10}$ each represent, independently, D-Leu, L-Leu, D-Ile or L-Ile, Xaa$_2$ and Xaa$_{11}$ each represent, independently, D-Asp, L-Asp, D-Glu or L-Glu, Xaa$_3$ represents D-Thr, L-Thr, D-allo-Thr or L-allo-Thr, Xaa$_6$ and Xaa$_8$ each represent, independently, D-Ser, L-Ser, D-Gln or L-Gln, the hydroxyl group of the Xaa$_3$ amino acid residue forms an ester bond with the C-terminal carboxyl group of the Xaa$_{11}$ amino acid residue, and $R_1$ represents the group of formula (I') below:

where $R_1'$ is a saturated alkyl chain of 5 to 8 carbon atoms, in particular 7 carbon atoms; and
(ii) at least one derivative of arthrofactin A, said derivative being of formula (II) below:

R-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$ (II)

in which
Xaa$_1$, Xaa$_4$, Xaa$_5$, Xaa$_7$, Xaa$_9$ and Xaa$_{10}$ each represent, independently, D-Leu, L-Leu, D-Ile or L-Ile,
Xaa$_2$ and Xaa$_{11}$ each represent, independently, D-Asp, L-Asp, D-Glu or L-Glu,
Xaa$_3$ represents D-Thr, L-Thr, D-allo-Thr or L-allo-Thr,
Xaa$_6$ and Xaa$_8$ each represent, independently, D-Ser, L-Ser, D-Gln or L-Gln,
the hydroxyl group of the Xaa$_3$ amino acid residue forms an ester bond with the C-terminal carboxyl group of the Xaa$_{11}$ amino acid residue, and
R represents the group of formula (II') below:

where R' is a hydrocarbon chain of 5 to 9 carbon atoms, optionally comprising at least one ethylenic unsaturation of cis or trans configuration.

Within the context of the invention, the amino acids preceded by the symbol "D-" are amino acids of D configuration, whilst the amino acids preceded by the symbol "L-" are amino acids of L configuration.

The term "D-allo-Thr" denotes the stereoisomer of threonine of (2R, 3R) configuration, whilst the term "L-allo-Thr" denotes the stereoisomer of threonine of (2S, 3S) configuration.

An "alkyl chain" is understood here to mean a saturated hydrocarbon chain.

In one particular embodiment, the $R_1'$ group as defined above is an alkyl chain of 5, 6, 7 or 8 carbon atoms and preferably is an alkyl chain of 7 carbon atoms.

In one particular embodiment, the R' group is a hydrocarbon chain of 5, 6, 7, 8 or 9 carbon atoms, optionally comprising at least one ethylenic unsaturation of cis or trans configuration. In one particular embodiment, the R' group as defined above is a saturated alkyl chain of 5, 6, 7, 8 or 9 carbon atoms. In another embodiment, the R' group is a hydrocarbon chain of 5, 6, 7, 8 or 9 carbon atoms comprising at least one ethylenic unsaturation of cis or trans configuration, preferably comprising exactly one ethylenic unsaturation of cis or trans configuration.

In one particular embodiment, the R' group is an alkyl chain of 7 or 9 carbon atoms, optionally comprising at least one ethylenic unsaturation of cis or trans configuration. In one particular embodiment, the R' group is a saturated alkyl chain of 7 or 9 carbon atoms. In another embodiment, the R' group is an alkyl chain of 7 or 9 carbon atoms comprising at least one ethylenic unsaturation of cis or trans configuration, preferably comprising exactly one ethylenic unsaturation of cis or trans configuration.

In one particular embodiment, the R' group is a saturated alkyl chain of 7 carbon atoms. In another particular embodiment, the R' group is a hydrocarbon chain of 7 carbon atoms comprising at least one ethylenic unsaturation of cis or trans configuration, preferably comprising exactly one ethylenic unsaturation of cis or trans configuration.

In another particular embodiment, the R' group is a saturated alkyl chain of 9 carbon atoms. In another particular embodiment, the R' group is a hydrocarbon chain of 9 carbon atoms comprising at least one ethylenic unsaturation of cis or trans configuration, preferably comprising exactly one ethylenic unsaturation of cis or trans configuration.

In one particular embodiment, the Xaa$_1$, Xaa$_4$, Xaa$_5$, Xaa$_7$, Xaa$_9$ and Xaa$_{10}$ amino acids as defined above each represent, independently, D-Leu or L-Leu. In another particular embodiment, the Xaa$_1$, Xaa$_4$, Xaa$_5$, Xaa$_7$, Xaa$_9$ and Xaa$_{10}$ amino acids each represent, independently, D-Ile or L-Ile.

In another embodiment, the Xaa$_1$, Xaa$_4$ and Xaa$_5$ amino acids each represent, independently, D-Leu or D-Ile. In another particular embodiment, the Xaa$_7$, Xaa$_9$ and Xaa$_{10}$ amino acids each represent, independently, L-Leu or L-Ile.

In a preferred embodiment, the Xaa$_1$, Xaa$_4$ and Xaa$_5$ amino acids each represent D-Leu. In another preferred embodiment, the Xaa$_7$ amino acid represents L-Leu. In another preferred embodiment, the Xaa$_9$, and Xaa$_{10}$ amino acids each represent L-Ile.

In one particularly preferred embodiment, the Xaa$_1$, Xaa$_4$ and Xaa$_5$ amino acids each represent D-Leu, the Xaa$_7$ amino acid represents L-Leu, and the Xaa$_9$ and Xaa$_{10}$ amino acids each represent L-Ile.

In one particular embodiment, the Xaa$_2$ and Xaa$_{11}$ amino acids each represent, independently, D-Asp or L-Asp. In another particular embodiment, the Xaa$_2$ and Xaa$_{11}$ amino acids each represent, independently, D-Glu or L-Glu. In another particular embodiment, the Xaa$_2$ and Xaa$_{11}$ amino acids each represent, independently, D-Asp or D-Glu. In a preferred embodiment, the Xaa$_2$ amino acid represents D-Asp. In a preferred embodiment, the Xaa$_{11}$ amino acid represents L-Asp or L-Glu. In a more preferred embodiment, the Xaa$_2$ amino acid represents D-Asp and the Xaa$_{11}$ amino acid represents L-Asp or L-Glu.

In one particular embodiment, the Xaa$_3$ amino acid represents D-Thr or L-Thr. In another particular embodiment, the Xaa$_3$ amino acid represents D-allo-Thr or L-allo-Thr. In another particular embodiment, the Xaa$_3$ amino acid represents D-Thr or D-allo-Thr. In a preferred embodiment, the Xaa$_3$ amino acid represents D-allo-Thr.

In one particular embodiment, the Xaa$_6$ and Xaa$_8$ amino acids each represent, independently, D-Ser or L-Ser. In another particular embodiment, the Xaa$_6$ and Xaa$_8$ amino acids each represent, independently, D-Gln or L-Gln. In another embodiment, the Xaa$_6$ and Xaa$_8$ amino acids each represent, independently, D-Ser or D-Gln. In a preferred embodiment, the Xaa$_6$ and Xaa$_8$ amino acids each represent D-Ser.

Thus, in one particular embodiment, the at least one derivative of arthrofactin A is of formula (II) below:

R-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$ (II)

in which
Xaa$_1$, Xaa$_4$, Xaa$_5$, Xaa$_7$, Xaa$_9$ and Xaa$_{10}$ each represent, independently, D-Leu, L-Leu, D-Ile or L-Ile,
Xaa$_2$ and Xaa$_{11}$ each represent, independently, D-Asp, L-Asp, D-Glu or L-Glu,
Xaa$_3$ represents D-Thr, L-Thr, D-allo-Thr or L-allo-Thr,
Xaa$_6$ and Xaa$_8$ each represent, independently, D-Ser, L-Ser, D-Gln or L-Gln,
the hydroxyl group of the Xaa$_3$ amino acid residue forms an ester bond with the C-terminal carboxyl group of the Xaa$_{11}$ amino acid residue, and
R represents the group of formula (II') below:

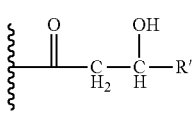
(II')

where R' is a saturated alkyl chain of 7 carbon atoms, a hydrocarbon chain of 7 carbon atoms comprising exactly one ethylenic unsaturation of cis or trans configuration, a saturated alkyl chain of 9 carbon atoms, or a hydrocarbon chain of 9 carbon atoms comprising exactly one ethylenic unsaturation of cis or trans configuration.

In another particular embodiment, the at least one derivative of arthrofactin A is of formula (II) below:

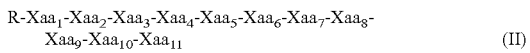

in which
Xaa$_1$, Xaa$_4$, Xaa$_5$, Xaa$_7$, Xaa$_9$ and Xaa$_{10}$ each represent, independently, D-Leu, L-Leu, D-Ile or L-Ile,
Xaa$_2$ and Xaa$_{11}$ each represent, independently, D-Asp, L-Asp, D-Glu or L-Glu,
Xaa$_3$ represents D-Thr, L-Thr, D-allo-Thr or L-allo-Thr,
Xaa$_6$ and Xaa$_8$ each represent, independently, D-Ser, L-Ser, D-Gln or L-Gln,
the hydroxyl group of the Xaa$_3$ amino acid residue forms an ester bond with the C-terminal carboxyl group of the Xaa$_{11}$ amino acid residue, and
R represents the group of formula (II') below:

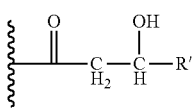
(II')

where R' is a saturated alkyl chain of 7 carbon atoms, a saturated alkyl chain of 9 carbon atoms, or a hydrocarbon chain of 9 carbon atoms comprising exactly one ethylenic unsaturation of cis or trans configuration.

In another particular embodiment, the at least one derivative of arthrofactin A is of formula (II) below:

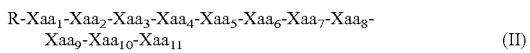

in which
Xaa$_1$, Xaa$_4$ and Xaa$_5$ each represent D-Leu, Xaa$_7$ represents L-Leu, and Xaa$_9$ and Xaa$_{10}$ each represent L-Ile, Xaa$_2$ represents D-Asp and Xaa$_{11}$ represents L-Asp or L-Glu,
Xaa$_3$ represents D-allo-Thr,
Xaa$_6$ and Xaa$_8$ each represent D-Ser
the hydroxyl group of the Xaa$_3$ amino acid residue forms an ester bond with the C-terminal carboxyl group of the Xaa$_{11}$ amino acid residue, and
R represents the group of formula (II') below:

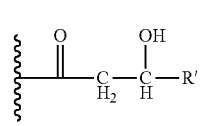
(II')

where R' is an alkyl chain of 5 to 9 carbon atoms, optionally comprising at least one ethylenic unsaturation of cis or trans configuration.

In another particular embodiment, the at least one derivative of arthrofactin A is of formula (II) below:

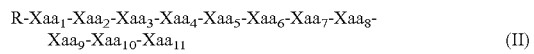

in which
Xaa$_1$, Xaa$_4$ and Xaa$_5$ each represent D-Leu, Xaa$_7$ represents L-Leu, and Xaa$_9$ and Xaa$_{10}$ each represent L-Ile,
Xaa$_2$ represents D-Asp and Xaa$_{11}$ represents L-Asp or L-Glu,
Xaa$_3$ represents D-allo-Thr,
Xaa$_6$ and Xaa$_8$ each represent D-Ser
the hydroxyl group of the Xaa$_3$ amino acid residue forms an ester bond with the C-terminal carboxyl group of the Xaa$_{11}$ amino acid residue, and
R represents the group of formula (II') below:

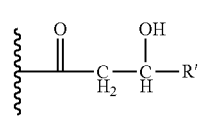
(II')

where R' is a saturated alkyl chain of 7 carbon atoms, a saturated alkyl chain of 9 carbon atoms, or a hydrocarbon chain of 9 carbon atoms comprising exactly one ethylenic unsaturation of cis or trans configuration.

In one particular embodiment, said at least one derivative of arthrofactin A is chosen from the group consisting of arthrofactin B, arthrofactin C, arthrofactin D and mixtures thereof,
arthrofactin B being of formula (III) below:

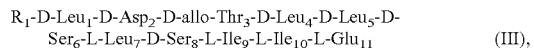

in which
the hydroxyl group of the D-allo-Thr$_3$ amino acid residue forms an ester bond with the C-terminal carboxyl group of the L-Glu$_{11}$ amino acid residue, and
R$_1$ is as defined in Claim 1;
arthrofactin C being of formula (IV) below:

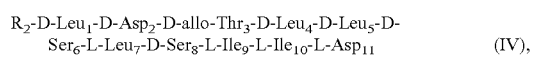

in which
the hydroxyl group of the D-allo-Thr$_3$ amino acid residue forms an ester bond with the C-terminal carboxyl group of the L-Asp$_{11}$ amino acid residue, and R$_2$ represents the group of formula (IV') below:

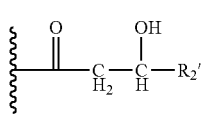
(IV')

where R$_2$' is an alkyl chain of 9 carbon atoms comprising exactly one unsaturation;
arthrofactin D being of formula (V) below:

R$_3$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$     (V), in which
the hydroxyl group of the D-allo-Thr$_3$ amino acid residue forms an ester bond with the C-terminal carboxyl group of the L-Asp$_{11}$ amino acid residue, and R$_3$ represents the group of formula (V') below:

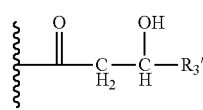
(V')

where R$_3$' is a saturated alkyl chain of 9 carbon atoms.

According to one particular embodiment of the invention, the mixture of arthrofactins having the anti-acne properties described here, is a mixture of arthrofactins comprising:

(i) arthrofactin A of formula (IA) below:

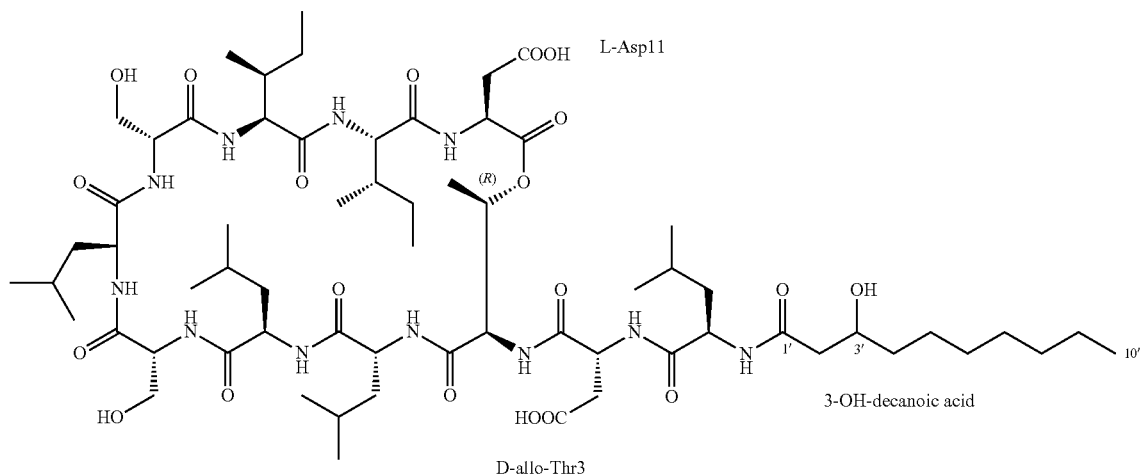

(ii) at least one derivative of arthrofactin A, said derivative being of formula (IIA) and/or (IIB) and/or (IIC) below:

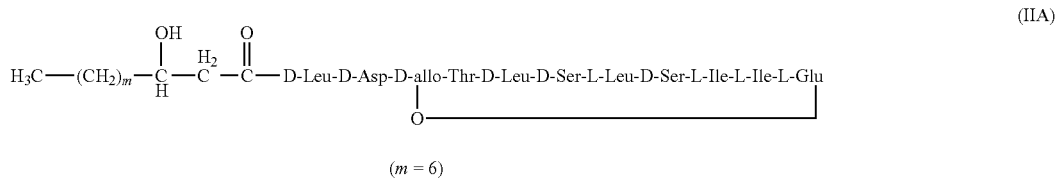
(IIA)

(m = 6)

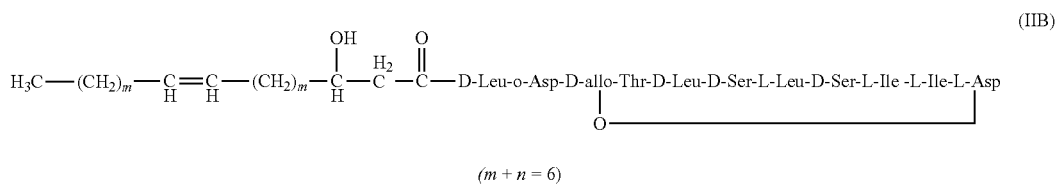
(IIB)

(m + n = 6)

(IIC)

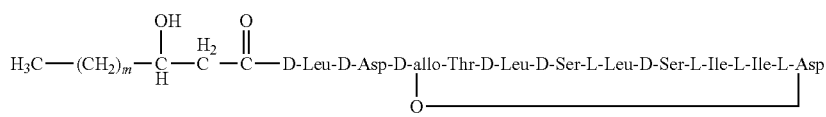

(m = 8)

According to one particular embodiment of the invention, the active ingredient of the composition according to the invention, having the properties, especially anti-acne properties, described here, is a mixture of arthrofactins comprising:
(i) arthrofactin A of formula (IA)
(ii) a derivative of arthrofactin A of formula (IIA)
(iii) a derivative of arthrofactin A of formula (IIB)
(iv) a derivative of arthrofactin A of formula (IIC)

The R, $R_1$, $R_2$ and $R_3$ groups as defined above are bonded to the N-terminal end of the $1^{st}$ amino acid (D-Leu$_1$ or Xaa$_1$) of the peptide sequence defined above.

In a particularly preferred embodiment of the invention, the arthrofactin mixture according to the invention predominantly comprises arthrofactin A.

The expression "to predominately comprise arthrofactin A" is understood here to mean that the arthrofactin A represents at least 50% by weight, preferably at least 60%, preferably at least 70%, of the mixture of arthrofactins, in particular of the assembly composed of arthrofactin A and derivatives of arthrofactin A as defined above.

The inventors have shown that the mixture of arthrofactins as defined above was typically obtained by fermentation with the *Pseudomonas* sp. MIS38 strain.

Thus, in one particular embodiment, the mixture of arthrofactins according to the invention is capable of being obtained by fermentation with the *Pseudomonas* sp. MIS38 strain.

The *Pseudomonas* sp. MIS38 strain is well known to a person skilled in the art and is for example described in Morikawa et al. (1993) *J. Bacteriol.* 175:6459-6466.

The mixture of arthrofactins according to the invention may be obtained by fermentation with the *Pseudomonas* sp. MIS38 strain, by any fermentation technique well known to a person skilled in the art, for example by the fermentation technique described in Washio et al. (2010) *Biosci. Biotechnol. Biochem.* 74:992-999. Typically, the *Pseudomonas* sp. MIS38 strain may be grown in the LB medium (1% Bacto tryptone, 0.5% yeast extract, 0.5% NaCl, pH 7.2) at 30° C. for 48 h. The culture may then be centrifuged and the supernatant recovered and concentrated, for example by ultrafiltration. The mixture of arthrofactins may then be purified from this supernatant by solid-phase extraction or liquid-liquid extraction.

The mixture of arthrofactins according to the invention may be obtained in particular according to the method described in ChemBioChem, 2012, 13, 2671-2675.

Composition

According to one particular embodiment of the invention, the cosmetic and/or pharmaceutical, in particular dermatological composition comprising at least one arthrofactin or a mixture of arthrofactins as described above is intended for topical administration to the skin and more particularly to the skin of the face.

The mixture of arthrofactins according to the invention may be present in the dermatological compositions according to the invention in an amount which may be between 0.01% and 10% by weight, preferably between 0.1% and 5% by weight, preferably between 0.5% and 3% by weight, more preferably between 1% and 2% by weight, relative to the total weight of the composition.

The composition additionally comprises a physiologically acceptable medium, i.e. a medium that has no unpleasant odour, colour or appearance, and that does not cause the user any discomfort such as unacceptable stinging or tautness. In particular, the composition is suitable for topical application to the skin.

A "physiologically acceptable medium" is thus understood to mean a medium that is compatible with human keratin materials and in particular with the skin of the body or of the face.

The composition according to the invention may comprise any of the cosmetic adjuvants normally used in the field of application envisioned.

The invention also relates to a composition comprising, in a physiologically acceptable medium, a mixture of arthrofactins as defined above and one or more additional active agents other than arthrofactin of formula (I) and arthrofactin derivatives of formula (II).

Galenical Forms

These compositions in which the compounds used according to the invention may be implemented are useful in particular for the care of the skin and particularly for treating acneic skin.

A composition used according to the invention is advantageously suitable for topical application to the skin.

For topical application to the skin, a composition according to the invention may be in any galenical form conventionally intended for this type of application and especially in the form of aqueous gels or aqueous or aqueous-alcoholic solutions. By adding a fatty or oily phase, they may also be in the form of dispersions of lotion type, emulsions of liquid or semi-liquid consistency of milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

Aqueous Phase

The compositions according to the invention intended for cosmetic use may comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of said compositions contains water and generally other water-soluble or water-miscible solvents. The water-soluble or water-miscible solvents comprise short-chain, for example $C_1$-$C_4$, monoalcohols such as ethanol and isopropanol; diols or polyols.

The compositions according to the invention preferably have a pH ranging from 3 to 9, depending on the chosen support.

When the composition(s) are in emulsion form, they generally contain, depending on the nature of the emulsion, one or more emulsifying surfactants.

The total amount of emulsifiers will preferably be, in the composition(s) according to the invention, in active material contents ranging from 1% to 8% by weight and more particularly from 2% to 6% by weight relative to the total weight of the composition.

Fatty Phase

The compositions according to the invention may contain at least one water-immiscible organic liquid phase, known as a fatty phase. This phase generally comprises one or more hydrophobic compounds which render said phase water-immiscible. Said phase is liquid (in the absence of structuring agent) at room temperature (20-25° C.). Preferentially, the water-immiscible organic liquid phase in accordance with the invention generally comprises at least one volatile oil and/or non-volatile oil and optionally at least one structuring agent.

The term "oil" means a fatty substance that is liquid at room temperature (25° C.) and atmospheric pressure (760 mmHg, i.e. $1.05 \times 10^5$ Pa). The oil may be volatile or non-volatile.

For the purposes of the invention, the term "volatile oil" means an oil that is capable of evaporating on contact with the keratin material, such as the skin, in less than one hour, at room temperature and atmospheric pressure. The volatile oils of the invention are volatile cosmetic oils, which are liquid at room temperature, having a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the keratin material, such as the skin, at room temperature and atmospheric pressure for at least several hours and that especially has a vapour pressure of less than $10^{-3}$ mmHg (0.13 Pa).

The oil may be chosen from any physiologically acceptable oil and in particular cosmetically acceptable oil, especially mineral, animal, plant or synthetic oils; in particular volatile or non-volatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oils that may be used in the invention, mention may be made of:

volatile hydrocarbon-based oils chosen from hydrocarbon-based oils containing from 8 to 16 carbon atoms, and especially $C_8$-$C_{16}$ isoalkanes of petroleum origin (also known as isoparaffins).

As examples of non-volatile oils that may be used in the invention, mention may be made of:

hydrocarbon-based plant oils such as liquid triglycerides of fatty acids of 4 to 24 carbon atoms, for instance caprylic/capric acid triglycerides such as those sold by the company Stéarineries Dubois or those sold under the names Miglyol 810, 812 and 818 by the company Dynamit Nobel, and jojoba oil, linear or branched hydrocarbons, of mineral or synthetic origin, such as liquid paraffins and derivatives thereof, petroleum jelly, polydecenes, polybutenes, hydrogenated polyisobutene such as Parleam, or squalane;

synthetic ethers having from 10 to 40 carbon atoms;

synthetic esters such as isononyl isononanoate, isopropyl myristate, isopropyl palmitate or $C_{12}$ to $C_{15}$ alkyl benzoate;

silicone oils such as linear (dimethicone) or cyclic (cyclomethicone) non-volatile polydimethylsiloxanes (PDMSs).

The compositions according to the invention may also comprise one or more adjuvants.

A person skilled in the art will take care to select this or these optional additional compounds such that the advantageous properties intrinsically associated with the composition in accordance with the invention are not, or are not substantially, adversely affected by the envisaged addition(s).

These optional adjuvants may be present in the composition in a proportion of from 0.001% to 80% by weight and in particular from 0.1% to 40% by weight relative to the total weight of the composition.

Depending on their nature, these adjuvants may be introduced into the fatty phase or into the aqueous phase of the composition or into lipid vesicles. In any case, these adjuvants, and the proportions thereof, will be chosen by those skilled in the art such that the advantageous properties of the mixture according to the invention are not, or are not substantially, adversely affected by the envisaged addition.

Hydrophilic gelling agents or thickeners that may be mentioned include carboxyvinyl polymers such as carbomer, acrylic copolymers such as acrylate/alkyl acrylate copolymers, polyacrylamides such as the mixture of polyacrylamide, C13-14 isoparaffin and laureth-7 sold under the name Sepigel 305$^e$ by the company SEPPIC, polysaccharides such as cellulose derivatives (for example hydroxyalkyl celluloses, in particular hydroxypropyl cellulose and hydroxyethyl cellulose), natural gums such as guar gum, locust bean gum and xanthan gum, and clays; lipophilic gelling agents or thickeners that may be mentioned include modified clays such as bentones, metal salts of fatty acids, hydrophobic silica, ethyl cellulose and polyethylene.

When the composition is an emulsion, the proportion of the fatty phase may be from 5% to 80% by weight and preferably from 8% to 50% by weight relative to the total weight of the composition. The emulsifier and the coemulsifier may be present in a proportion ranging from 0.3% to 30% by weight, preferably from 0.5% to 20% by weight relative to the total weight of the composition.

The composition according to the invention may be more or less fluid and may have the appearance of a white or coloured cream, an ointment, a milk, a lotion, a serum, a paste, a gel or a foam. It may optionally be applied in the form of an aerosol. It may also be in solid form, in particular in stick form. It may also be on a support, for example on wipes such as makeup remover wipes.

The expressions "between . . . and . . . " and "ranging from . . . to . . . " or "at least of . . . " should be understood to mean limits included, unless otherwise specified.

Throughout the text hereinbelow, the percentages are given on a weight basis, unless otherwise mentioned.

The examples that follow illustrate the invention, and are given purely as nonlimiting illustrations.

EXAMPLES

Example 1: Preparation of a Mixture of Arthrofactins According to the Invention The MIS38 strain was grown in a King'B medium at 28° C., 120 rpm and 4 vvm. At the end of the fermentation, the culture medium was clarified by centrifugation and the supernatant obtained was concentrated by ultrafiltration (MWCO 10 kDa). The control of the transmembrane pressure in an appropriate concentration range makes it possible to measure a concentration 7 times higher in the supernatant, this supernatant is then diafiltered twice in order to eliminate the residual contaminations of the culture medium. This fraction is then concentrated to dryness until a dry powder is obtained.

The fraction contains a mixture of arthofactin, in particular it contains arthrofactin A of formula (IA) below:

Example 2: The Arthrofactin Mixture According to the Invention has an Anti-Acne Property This example shows that the arthrofactin mixture according to the invention described in example 1 has an inhibitory activity on *Propionibacterium acnes*, which is responsible for acne.

The strain of *Propionibacterium acnes* ATCC 6919 initially kept at −20° C. in glycerol containing a culture broth was precultured in LB medium with stirring (160 rpm) at 30° C. After incubating for 16 hours, the cultures were centrifuged at 10 000 rpm for 5 min, and the cellular pellets were washed twice with PBS, before being inoculated at a concentration of $5 \times 10^9$ CFU per plate in a 100 mm diameter petri dish containing 20 m of reinforced medium (RCM) supplemented with 1.5% of agarose at supercooling temperature. After solidification, at least three 6 mm discs of filter paper were placed on the surface of the agar layer.

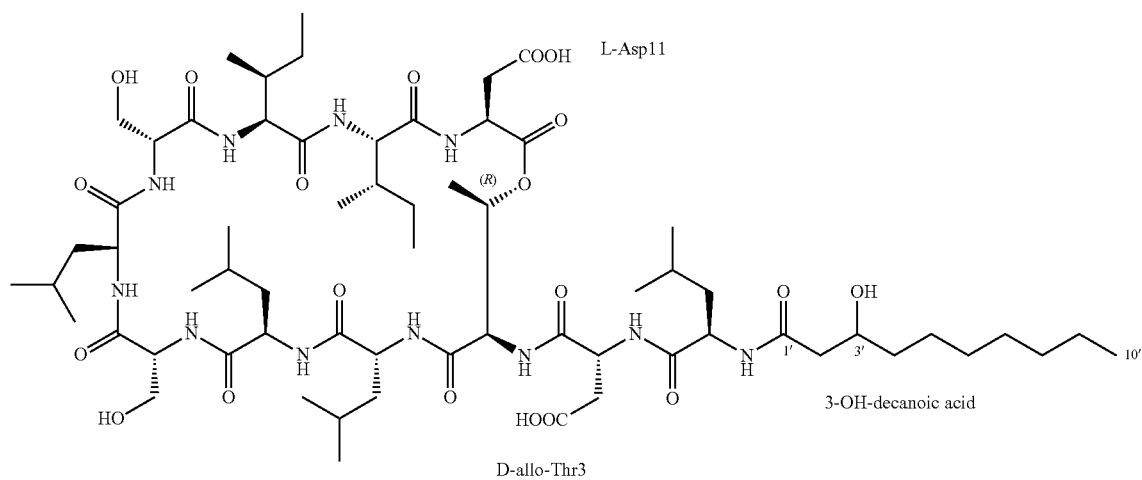

+3 arthrofactin A derivatives of formulae (IIA), (IIB), (IIC) below:

Control solutions and solutions of 0.5% and 1% of mixture of arthrofactins were prepared in a 1,3-propanediol/PBS

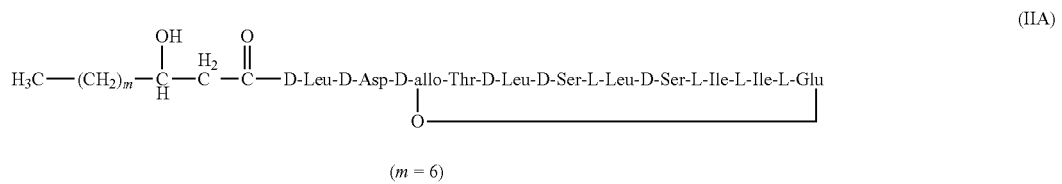

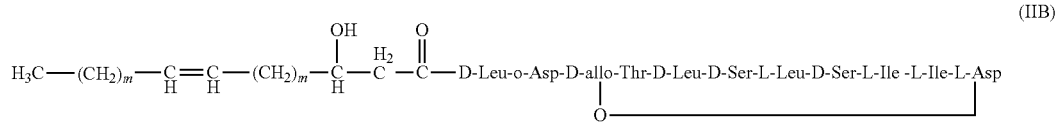

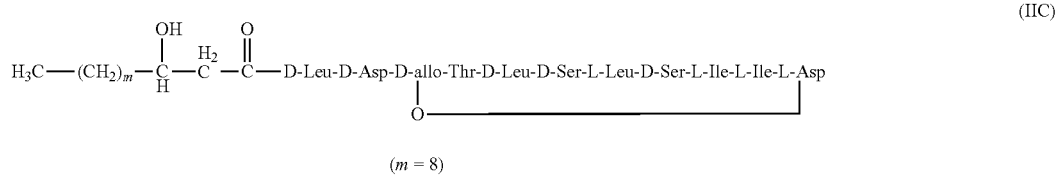

(1/1, v/v) vehicle. 10 μl of each sample to be tested were deposited on the discs. Lastly, the plates were incubated anaerobically for 72 h at 37° C.

At the end of the incubation period, the antagonist activity was measured as the diameter of the clear zone of growth inhibition and recorded as being the diameter of the inhibition zone in mm. 0.01% triclosan was used as positive control for the antibacterial activity and the vehicle served as negative control. Tests were carried out in triplicate.

An inhibitory activity of the arthrofactin mixture at 0.5% and 1% on the *P. acnes* strain is observed.

Example 3: Compositions for Topical Application

The following composition, for topical application, was prepared in the form of a cream:

|  | Weight % |
| --- | --- |
| Compound from Example 1 | 1% |
| Glyceryl monostearate | 0.8% |
| Cetyl alcohol | 2.0% |
| Stearyl alcohol | 5.0% |
| Polyoxyethylene (20 OE) stearate | 3.0% |
| Crosslinked acrylic acid (Carbopol 941) | 0.3% |
| Caprylic/capric triglycerides | 12.0% |
| Preservatives qs |  |
| Water qs | 100.0% |

This cream is applied once or twice a day to acneic skin. The exemplified formulation applied displays a good effect on acneic skin.

The invention claimed is:

1. A method for the treatment of acneic skin which comprises contacting the acneic skin with an effective amount of an arthrofactin mixture comprising
   (i) arthrofactin A of formula (I) below:

$R_1$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$ (I), in which
   the hydroxyl group of the D-allo-Thr$_3$ amino acid residue forms an ester bond with the C-terminal carboxyl group of the L-Asp$_{11}$ amino acid residue, and
   $R_1$ represents the group of formula (I') below:

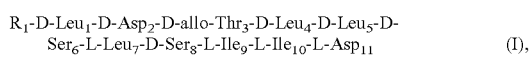
   (I')

where $R_1'$ is a saturated alkyl chain of 5 to 8 carbon atoms; and
   (ii) at least one derivative of arthrofactin A, said derivative being of formula (II) below:

R-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$ (II)

in which
   Xaa$_1$, Xaa$_4$, Xaa$_5$, Xaa$_7$, Xaa$_9$ and Xaa$_{10}$ each represent, independently, D-Leu, L-Leu, D-Ile or L-Ile,
   Xaa$_2$ and Xaa$_{11}$ each represent, independently, D-Asp, L-Asp, D-Glu or L-Glu,
   Xaa$_3$ represents D-Thr, L-Thr, D-allo-Thr or L-allo-Thr,
   Xaa$_6$ and Xaa$_8$ each represent, independently, D-Ser, L-Ser, D-Gln or L-Gln,
   the hydroxyl group of the Xaa$_3$ amino acid residue forms an ester bond with the C-terminal carboxyl group of the Xaa$_{11}$ amino acid residue, and
   R represents the group of formula (II') below:

   (II')

where R' is an alkyl chain of 5 to 9 carbon atoms, optionally comprising at least one unsaturation.

2. The method according to claim 1, in which the acneic skin has imperfections related to *Propionibacterium acnes*.

3. The method according to claim 1, which comprises inhibiting the growth of *Propionibacterium acnes*.

4. The method according to claim 1, in which $R_1'$ is a saturated alkyl chain of 7 carbon atoms.

5. The method according to claim 1, in which the at least one derivative of arthrofactin A is chosen from the group consisting of arthrofactin B, arthrofactin C, arthrofactin D and mixtures thereof,
   arthrofactin B being of formula (III) below:

R-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Glu$_{11}$ (III), in which
   the hydroxyl group of the D-allo-Thr$_3$ amino acid residue forms an ester bond with the C-terminal carboxyl group of the L-Glu$_{11}$ amino acid residue, and
   arthrofactin C being of formula (IV) below:

$R_2$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$ (IV), in which
   the hydroxyl group of the D-allo-Thr$_3$ amino acid residue forms an ester bond with the C-terminal carboxyl group of the L-Asp$_{11}$ amino acid residue, and
   $R_2$ represents the group of formula (IV') below:

   (IV')

where $R_2'$ is an alkyl chain of 9 carbon atoms comprising exactly one unsaturation;
   arthrofactin D being of formula (V) below:

$R_3$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$ (V), in which
   the hydroxyl group of the D-allo-Thr$_3$ amino acid residue forms an ester bond with the C-terminal carboxyl group of the L-Asp$_{11}$ amino acid residue, and $R_3$ represents the group of formula (V') below:

where $R_3'$ is a saturated alkyl chain of 9 carbon atoms.

6. The method according to claim 1, in which the arthrofactin mixture comprises
(iii) arthrofactin A of formula (IA) below:

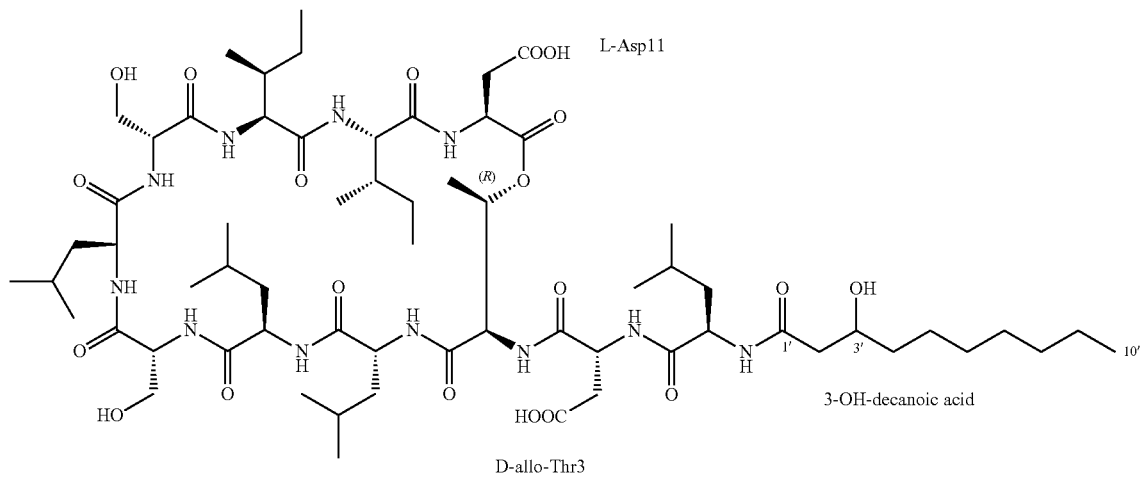

(iv) at least one derivative of arthrofactin A chosen from the compounds of formula (IIA), (IIB) and/or (IIC) of formula(e) below:

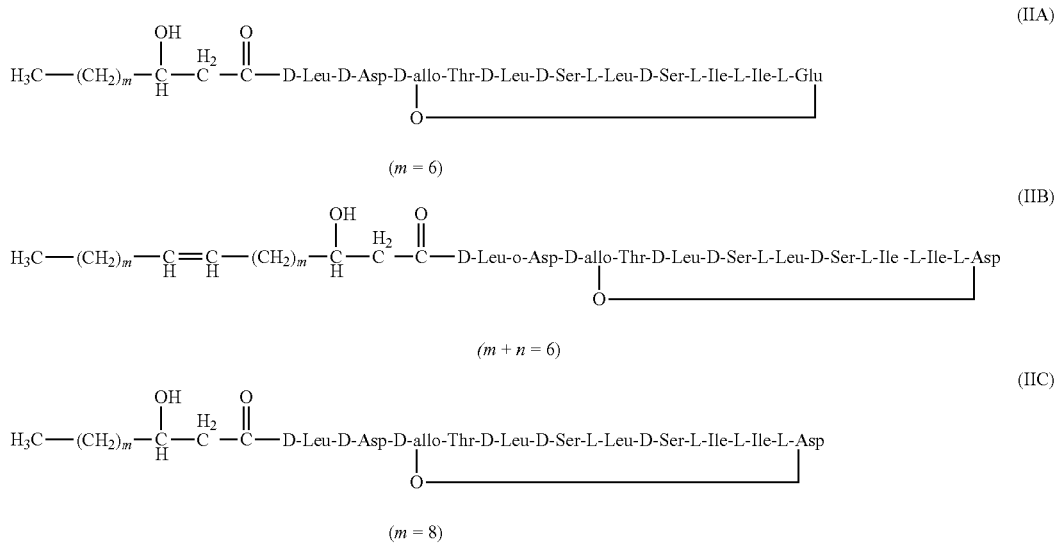

7. The method according to claim 1, in which the at least one derivative of arthrofactin A is a mixture of the compounds of formula (IIA), (IIB) and (IIC).

8. The method according to claim 1, in which the arthrofactin mixture predominantly comprises arthrofactin A.

9. The method according to claim 1, in which the arthrofactin mixture is obtained by fermentation with the *Pseudomonas* sp. MIS38 strain.

10. The method according to claim 1, which comprises repeatedly applying the arthrofactin mixture to the acneic skin daily over a period of at least one week.

11. The method according to claim 10, which comprises repeatedly applying the arthrofactin mixture to the acneic skin daily over a period of at least four weeks.

12. The method according to claim 10, which comprises repeatedly applying the arthrofactin mixture to the acneic skin at least twice daily.

13. The method according to claim 1, wherein the arthrofactin mixture is in the form of a dermatological composition comprising a physiologically acceptable medium and at least one compound chosen from thickeners, preservatives, fragrances, bactericides, pigments, colorants, organic solvents, carbon-based and/or silicone oils, waxes, fillers, emulsifiers, co-emulsifiers, UV screening agents, polymers, and hydrophilic or lipophilic gelling agents.

14. The method according to claim 1, comprising a physiologically acceptable medium and at least one compound chosen from thickeners, preservatives, fragrances, bactericides, $C_1$-$C_6$ alcohols, $C_2$-$C_{10}$ carboxylic acid esters, and carbon-based and/or silicone oils.

15. The method according to claim 2, in which the at least one derivative of arthrofactin A is chosen from the group consisting of arthrofactin B, arthrofactin C, arthrofactin D and mixtures thereof, arthrofactin B being of formula (III) below:

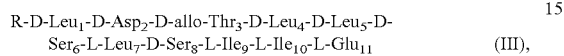

R-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Glu$_{11}$   (III), in which
the hydroxyl group of the D-allo-Thr$_3$ amino acid residue forms an ester bond with the C-terminal carboxyl group of the L-Glu$_{11}$ amino acid residue;

arthrofactin C being of formula (IV) below:

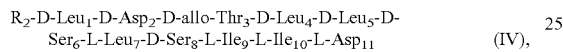

R$_2$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$   (IV), in which
the hydroxyl group of the D-allo-Thr$_3$ amino acid residue forms an ester bond with the C-terminal carboxyl group of the L-Asp$_{11}$ amino acid residue, and $R_2$ represents the group of formula (IV') below:

where $R_2'$ is an alkyl chain of 9 carbon atoms comprising exactly one unsaturation;

arthrofactin D being of formula (V) below:

R$_3$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$   (V),

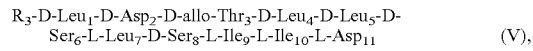

in which
the hydroxyl group of the D-allo-Thr$_3$ amino acid residue forms an ester bond with the C-terminal carboxyl group of the L-Asp$_{11}$ amino acid residue, and $R_3$ represents the group of formula (V') below:

where $R_3'$ is a saturated alkyl chain of 9 carbon atoms.

16. The method according to claim 1, in which the arthrofactin mixture comprises
(iii) arthrofactin A of formula (IA) below:

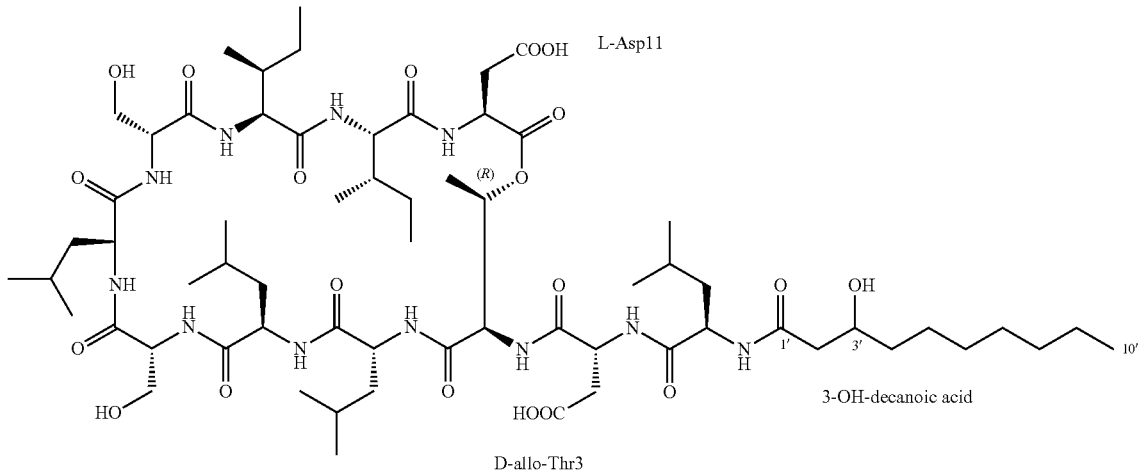

(iv) at least one derivative of arthrofactin A chosen from the compounds of formula (IIA), (IIB) and/or (IIC) of formula(e) below:

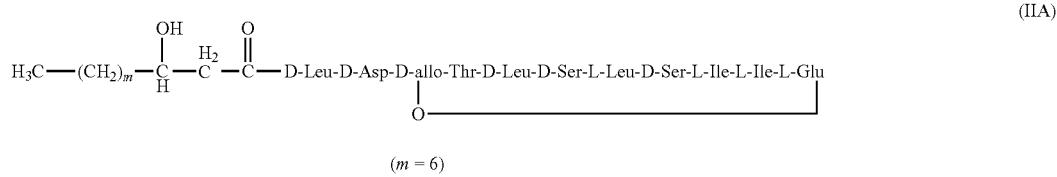

(m = 6)

-continued

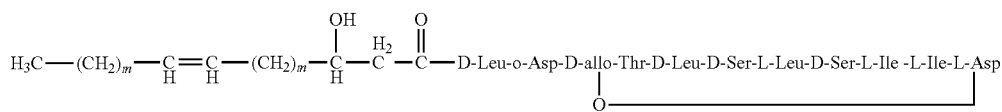

(m + n = 6)

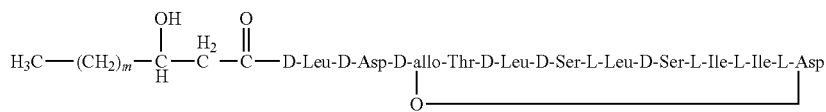

(m = 8)

17. The method according to claim 2, in which the arthrofactin mixture comprises
(iii) arthrofactin A of formula (IA) below:

18. The method according to claim 2, in which the at least one derivative of arthrofactin A is a mixture of said compounds of formula (IIA), (IIB) and (IIC).

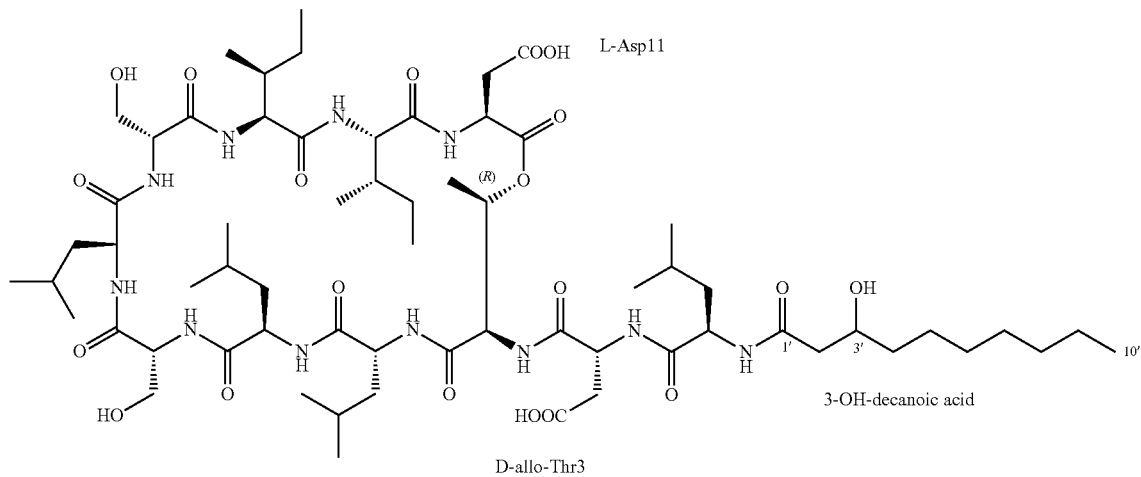

(iv) at least one derivative of arthrofactin A chosen from the compounds of formula (IIA), (IIB) and/or (IIC) of formula(e) below:

19. The method according to claim 3, in which the at least one derivative of arthrofactin A is a mixture of said compounds of formula (IIA), (IIB) and (IIC).

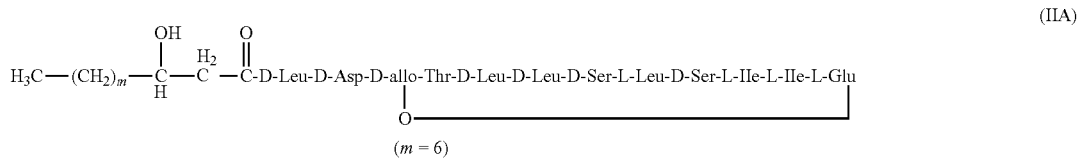

(m = 6)

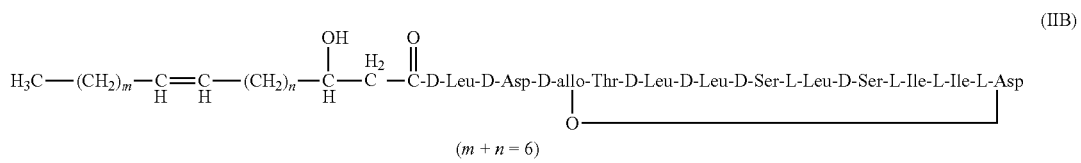

(m + n = 6)

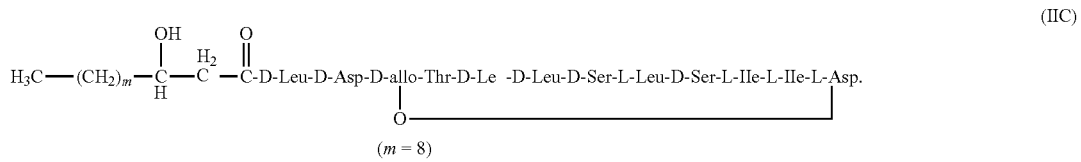

(m = 8)

20. The method according to claim 10, in which said at least one derivative of arthrofactin A is a mixture of said compounds of formula (IIA), (IIB) and (IIC).

\* \* \* \* \*